(12) United States Patent
Vu et al.

(10) Patent No.: US 8,889,915 B2
(45) Date of Patent: Nov. 18, 2014

(54) METHODS AND SYSTEMS FOR SEPARATING ACETONE AND PHENOL FROM ONE ANOTHER

(71) Applicant: Kellogg Brown & Root LLC, Houston, TX (US)

(72) Inventors: Truc Vu, Houston, TX (US); Theodor Robert Wilks, Sugar Land, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 0 days.

(21) Appl. No.: 14/189,291

(22) Filed: Feb. 25, 2014

(65) Prior Publication Data

US 2014/0275630 A1    Sep. 18, 2014

Related U.S. Application Data

(60) Provisional application No. 61/783,587, filed on Mar. 14, 2013.

(51) Int. Cl.

| | | |
|---|---|---|
| C07C 45/53 | (2006.01) | |
| C07C 37/08 | (2006.01) | |
| C07C 45/82 | (2006.01) | |
| B01D 3/26 | (2006.01) | |
| C07C 37/74 | (2006.01) | |
| C07C 407/00 | (2006.01) | |
| C07C 7/04 | (2006.01) | |

(52) U.S. Cl.
CPC . *C07C 45/82* (2013.01); *B01D 3/26* (2013.01); *C07C 37/74* (2013.01); *C07C 407/00* (2013.01); *C07C 45/53* (2013.01); *C07C 7/04* (2013.01)
USPC ........... 568/385; 568/410; 568/798; 568/810; 422/187

(58) Field of Classification Search
CPC ...... C07C 45/53; C07C 37/08; B01J 2219/00; B01J 8/00
USPC .................. 568/385, 410, 798, 810; 422/187
See application file for complete search history.

(56) References Cited

U.S. PATENT DOCUMENTS

| | | | | |
|---|---|---|---|---|
| 4,340,447 A | * | 7/1982 | Laverick et al. ................. | 203/36 |
| 5,371,305 A | * | 12/1994 | Hood ............................ | 568/798 |
| 7,381,854 B2 | * | 6/2008 | Birkhoff et al. ............... | 585/265 |

* cited by examiner

*Primary Examiner* — Sikarl Witherspoon
(74) *Attorney, Agent, or Firm* — Gary M. Machetta

(57) ABSTRACT

Systems and methods for improving crude acetone column energy efficiency and operation are provided. The method for improving crude acetone column energy efficiency and operation can include introducing a crude acetone including acetone and phenol to a fractionation column and introducing cumene, AMS, or a combination thereof to the fractionation column. The method can include fractionating the crude acetone within the fractionation column to produce an acetone containing overhead and a phenol containing bottoms. The method can also include condensing at least a portion of the acetone containing overhead indirectly with a cool heat transfer medium to provide a condensed crude acetone product and a heated heat transfer medium, wherein the heat transfer medium includes cumene.

20 Claims, 2 Drawing Sheets

METHODS AND SYSTEMS FOR SEPARATING ACETONE AND PHENOL FROM ONE ANOTHER

BACKGROUND

1. Field

Embodiments described herein generally relate to methods and systems for producing phenol and acetone from cumene. More particularly, such embodiments relate to methods and systems for separating acetone from phenol in a crude acetone column of a phenol production process.

2. Description of the Related Art

Phenol and acetone are produced in various processes, the most common of which is known variously as the Hock Process, the Hock and Lang Process, or the cumene-to-phenol process, among others. This process begins with the oxidation of cumene (isopropyl benzene) to form cumene hydroperoxide (CHP). The CHP is then cleaved in the presence of an acid catalyst to form a phenol, acetone, and/or alpha-methyl styrene ("AMS") mixture. The mixture is subsequently neutralized and fractionated to recover the end-products phenol, acetone, and/or AMS.

During the fractionation of a phenol and acetone mixture, unstable operation is often experienced. For example, a typical crude acetone column design cools overhead vapor by partially condensing the overhead vapor in a crude acetone column condenser by either tempered water or air. Such cooling mediums lead to unstable operation and fouling associated with water systems.

There is a need, therefore, for improved methods and systems for separating acetone and phenol in an acetone/phenol mixture.

DETAILED DESCRIPTION

Systems and methods for improving crude acetone column energy efficiency and operation are provided. The method for improving crude acetone column energy efficiency and operation can include introducing a crude acetone including acetone and phenol to a fractionation column and introducing cumene, AMS, or a combination thereof to the fractionation column. The method can include fractionating the crude acetone within the fractionation column to produce an acetone containing overhead and a phenol containing bottoms. The method can also include condensing at least a portion of the acetone containing overhead indirectly with a cool heat transfer medium to provide a condensed crude acetone product and a heated heat transfer medium, wherein the heat transfer medium includes cumene.

As used herein, the terms "fractionation column" and "column" refer to any system, device, or combination of systems and/or devices suitable for the separation of a mixture containing two or more components having differing boiling points. Such fractionation columns can include, but are not limited to, dividing wall columns, scrub columns, distillation columns, rectification columns, and stripping columns.

As used herein, the terms "light products," "light components," "light molecules," "heavy products," "heavy components," and "heavy molecules" denote "low-boiling" and "high-boiling," products, components, and molecules, respectively, for a given set of two or more compounds. Unless otherwise mentioned, "light" and "heavy" refer to respective boiling points and do not necessarily denote actual molecular-weight comparisons.

Figure 1:
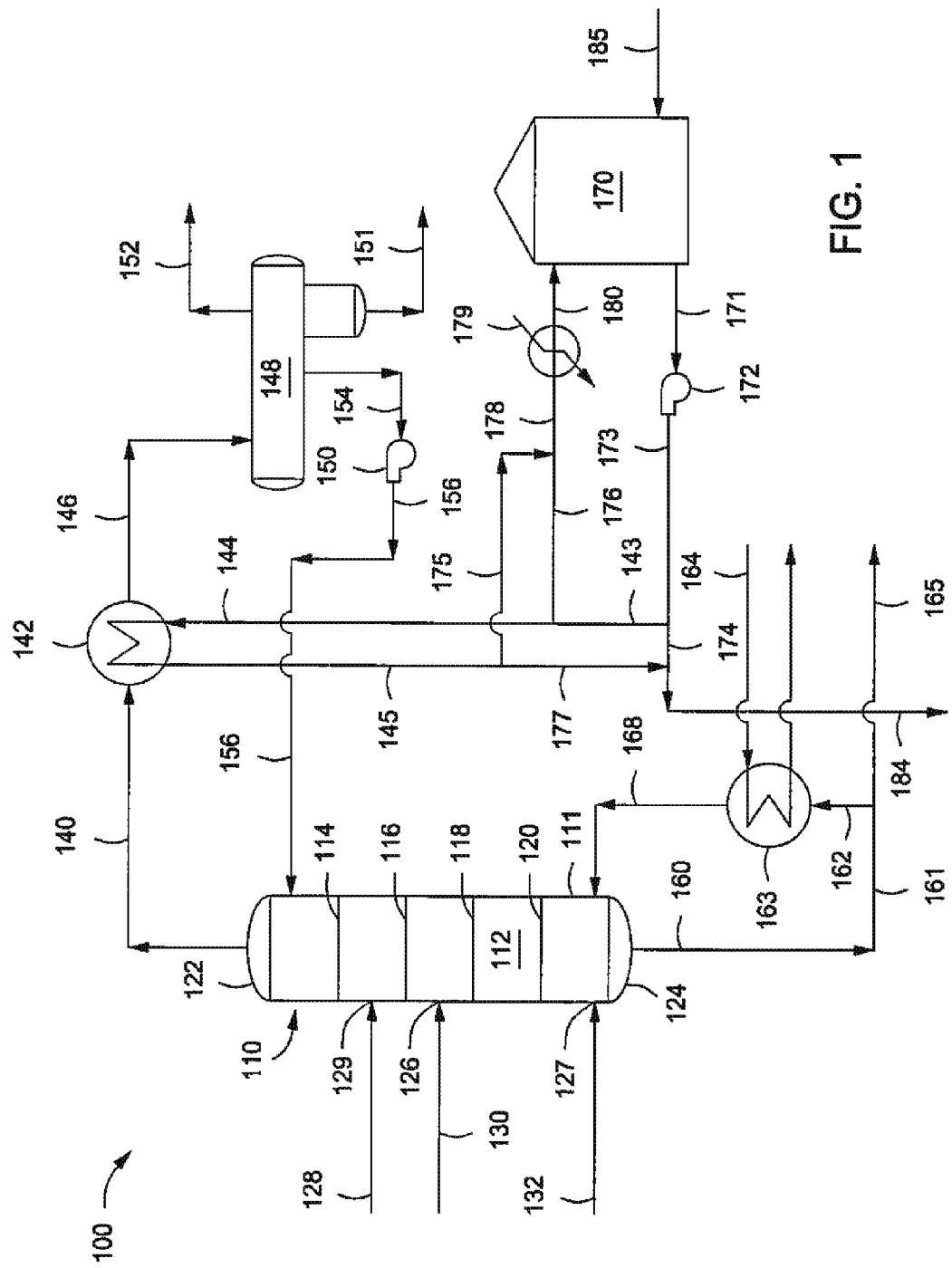
FIG. 1 depicts an illustrative fractionation system for fractionating a crude acetone product, according to one or more embodiments described.

FIG. 1 depicts an illustrative fractionation system 100 for fractionating an acetone or "crude" acetone product in line 130, according to one or more embodiments. The system 100 can include one or more fractionation columns 110. The fractionation column 110 (or "crude acetone column" ("CAC")) can include a shell or housing 111 disposed at any angle, in any configuration, and/or having any length to average cross-sectional length, e.g., diameter, ratio. For clarity and ease of description, the fractionation column 110 will be further described with reference to a vertical, cylindrical, fractionation column 110 having a length to diameter (L/D) ratio greater than 1.

The fractionation column 110 can have a first or "top" end 122 and a second or "bottom" end 124. The fractionation column 110 can include one or more trays, random packing, or structured packing sections (Four are shown, 114, 116, 118, 120) disposed within the housing 111. The crude acetone product via line or "first input line" 130 can be introduced into an interior or internal volume 112 of the fractionation column 110 via a first column inlet 126. The crude acetone product in line 130 can be neutralized. A cumene and/or alpha-methyl styrene ("AMS") containing feed via line 132 can be introduced into the internal volume 112 of the fractionation column 110 at a location below the inlet of the crude acetone product, for example via a second column inlet 127. For example, the cumene and/or AMS can be introduced to the fractionation column 110 below the first inlet 126 of the crude acetone product in line 130 and at a location proximate the bottom end 124 of the fractionation column 110. It has been found that introducing the cumene and/or AMS via line 132 to the fractionation column 110 below the inlet of the crude acetone product in line 130 can enhance the amount of hydroxyacetone recovered in a column overhead via line or "column overhead line," 140 fluidly coupled to the fractionation column 110. It has also been found that introduction of the cumene and/or AMS via line 132 below the inlet of the crude acetone product in line 130 can significantly reduce a column reflux and reboiler duty.

The fractionation column 110 can be heated to provide or produce a thermal gradient within the internal volume 112 between the first and second ends 122, 124 thereof. The components with lower boiling points of the crude acetone product can be directed toward the first end 122 and components with higher boiling points can be directed toward the second end 124. The lighter boiling point components can include acetone, water, cumene, and/or AMS, and can be recovered in a column overhead via line 140. The heavier boiling point components can include phenol and can be recovered in a bottoms stream or "bottoms line," 160 fluidly coupled to the fractionation column 110.

The crude acetone product in line 130 can have a pH from about 4 to about 7. For example, the crude acetone product can have a pH from a low of about 4.5 to a high of about 5. In another example, the pH of the crude acetone product can be about 4 to about 6, about 4.5 to about 5.5, or about 4.25 to about 5. If desired, the pH of the crude acetone product can be adjusted prior to being fed to the column via the addition of one or more acids and/or one or more bases. For example, the crude acetone product in line 130 can be neutralized by adding one or more base compounds. Suitable base compounds for neutralizing the crude acetone product can include, but are not limited to, amine, ammonia, sodium hydroxide, sodium phenate or any combination thereof. A suitable acid that can be added to the crude acetone product to adjust the pH thereof can be or include sulfuric acid. The pH of the crude acetone product in line 130 can also be adjusted by contacting the crude acetone product with one or more ion exchange resins. Illustrative ion exchange resins can include, but are not limited to, macroporous phenolic weak base resins, gel-type acrylic weak base resins, macroporous styrenic weak base resins, or any combination thereof.

In addition to acetone, the crude acetone product in line 130 can include, but is not limited to, phenol, mesityl-oxide, 2-methylbenzofuran, alpha-methyl styrene (AMS), cumene, hydroxyacetone, alpha-methyl styrene dimers, ethylbenzene, n-propylbenzene, sec-butylbenzene, tert-butylbenzene, para-cumyl phenol, water, phenyl dimethyl carbinol (carbinol), acetophenone, higher boiling hydrocarbons, or any combination thereof. The crude acetone product in line 130 can have a phenol concentration from a low of about 30 wt %, about 35 wt %, or about 40 wt % to a high of about 50 wt %, about 55 wt %, or about 60 wt %. The crude acetone product in line 130 can have an acetone concentration from a low of about 25 wt %, about 30 wt %, or about 35 wt % to a high of about 40 wt %, about 45 wt %, or about 50 wt %. The crude acetone product in line 130 can have an AMS concentration from a low of about 1.5 wt %, about 2 wt %, or about 2.5 wt % to a high of about 3 wt %, about 4 wt %, or about 6 wt %. The crude acetone product in line 130 can have a cumene concentration from a low of about 4 wt %, about 6 wt %, or about 8 wt % to a high of about 10 wt %, about 20 wt %, or about 30 wt %. The crude acetone product in line 130 can have a hydroxyacetone concentration from a low of about 10 parts per million by weight (ppmw), about 100 ppmw, or about 200 ppmw to a high of about 500 ppmw, about 1000 ppmw, or about 2000 ppmw. The crude acetone product in line 130 can have a water concentration from a low of about 2 wt %, about 4 wt %, or about 6 wt % to a high of about 8 wt %, about 12 wt %, or about 15 wt %.

The crude acetone product via line 130 can be introduced to the fractionation column 110 at a pressure ranging from a low of about 50 kPa, about 75 kPa, about 100 kPa, or about 115 kPa to a high of about 125 kPa, about 135 kPa, about 150 kPa, or about 200 kPa. The crude acetone product in line 130 can be at a temperature ranging from a low of about 20° C., about 30° C., about 45° C., about 60° C. or about 70° C. to a high of about 80° C., about 100° C., about 110° C., about 125° C., or about 150° C.

In one or more embodiments, both the overhead stream 140 and the bottoms stream 160 can contain hydroxyacetone. In one example, the bottoms stream 160 can contain a greater amount of hydroxyacetone than the overhead stream 140. In another example, the overhead stream 140 can contain a greater amount of hydroxyacetone than the bottoms steam 160. For example, at least about 10%, at least about 20%, at least about 30%, at least about 40%, at least about 50%, at least about 60%, at least about 70%, at least about 80%, at least about 90%, at least about 95%, or 100% of the hydroxyacetone present in the crude acetone product and the cumene and/or AMS containing stream can be removed as a component in the overhead stream 140. In another example, the mount of the hydroxyacetone present in the overhead stream 140 can be from about 60% to about 98%, about 70% to about 95%, about 80% to about 90%. In one or more embodiments, the overhead 140 can be substantially free of hydroxyacetone. For example, the overhead 140 can contain less than about 10 wt %, less than about 5 wt %, less than about 1 wt %, or less than about 0.1 wt % hydroxyacetone.

The first column inlet 126 can be positioned at any height along the fractionation column 110. For example, the first column inlet 126 can be located above the trays 114, 116, 118, 120. In another example, the first column inlet 126 can be located below the trays 114, 116, 118. In another example, the first column inlet can be located between trays 114 and 116, between trays 116 and 118, or between trays 118 and 120. In one example, the tray 116 can represent the $15^{th}$ tray of an approximately 65 tray fractionation column 110 with the $1^{st}$ tray being located at the top or first end 122 and the $65^{th}$ tray being located at bottom or second end 124. In another example, the tray 116 can represent the $10^{th}$, $12^{th}$, $13^{th}$, $14^{th}$, $15^{th}$, $16^{th}$, $17^{th}$, or $18^{th}$ tray of an approximately 65 tray fractionation column 110. In yet another example, the trays 114, 116, 118, 120 can be part of a stack of trays, random packing, or structured packing.

The crude acetone product in line 130 can be introduced to the fractionation column 110 at multiple locations along the fractionation column 110. For example, in addition to the first column inlet 126, the crude acetone product in line 130 can also be introduced at one or more locations along the fractionation column 110 above the first column inlet 126. In another example, the crude acetone product in line 130 can also be introduced at one or more locations along the fractionation column 110 between the first column inlet 126 and the second end 124 of the fractionation column 130. In another example, the crude acetone product in line 130 can also be introduced at one or more locations along the fractionation column 110 between the first column inlet 126 and the first end 122 of the fractionation column 130.

The crude acetone product in line 130 can be introduced to the fractionation column 110 as a liquid and/or as a vapor. For example, the amount of the crude acetone product in line 130 that can be vaporized when introduced to the fractionation column 110 can be from a low of about 1 wt %, about 5 wt %, about 10 wt %, about 20 wt %, or about 30 wt % to a high of about 50 wt %, about 60 wt %, about 75 wt %, about 85 wt %, about 90 wt %, or about 99 wt %.

The amount of cumene and/or AMS introduced to the fractionation column 110 via line 132 can determine, at least in part, the reflux ratio of the fractionation column 110 and/or the reboiler duty. In one or more embodiments, the amount of cumene and/or AMS introduced to the fractionation column 110 via line 132 can determine, at least in part, the amount of hydroxyacetone present in the bottoms product via line 160.

The AMS and/or cumene feed via line 132 can be introduced to the fractionation column 110 at a pressure from a low of about 50 kPa, about 75 kPa, about 100 kPa, or about 115 kPa to a high of about 125 kPa, about 135 kPa, about 150 kPa, or about 200 kPa. The AMS and/or cumene feed via line 132 can be at a temperature from a low of about 20° C., about 30° C., about 30° C., about 40° C. or about 50° C. to a high of about 55° C., about 60° C., about 65° C., about 70° C., or about 80° C. The AMS and/or cumene feed via line 132 can have a concentration of cumene from a low of about 1 wt %, about 5 wt %, about 10 wt %, about 15 wt %, or about 20 wt % to a high of about 70 wt %, about 80 wt %, about 90 wt %, about 95 wt %, about 99 wt % or more, based on the combined weight of AMS and cumene. The AMS and/or cumene feed via line 132 can have a concentration of AMS from a low about 1 wt %, about 5 wt %, about 10 wt %, about 15 wt %, or about 20 wt % to a high of about 70 wt %, about 80 wt %, about 90 wt %, about 95 wt %, about 99 wt % or more, based on the combined weight of AMS and cumene. For example, the feed via line 132 can include about 60 wt % to about 90 wt % cumene and about 10 wt % to about 40 wt % AMS. In another example, the feed via line 132 can include about 70 to about 90 wt % cumene and about 10 wt % to about 30 wt % AMS. In another example, the feed via line 132 can include about 75 wt %, about 80 wt %, or about 85 wt % cumene and about 25 wt %, about 20 wt %, or about 15 wt % AMS, respectively.

The weight ratio of the AMS and/or cumene feed in line 132 to the crude acetone product in line 130 introduced to the fractionation column 110 can be at least about 1:50, at least about 1:30, at least about 1:20, at least about 1:15, at least about 1:10, or at least about 1:5. For example, the weight ratio of the AMS and/or cumene feed in line 132 to the crude acetone product in line 130 introduced to the fractionation column 110 can range from about 1:50 to about 1:15, from about 1:50 to about 1:25, from about 1:50 to about 1:35, or from about 1:40 to about 1:15.

Water via line 128 can be introduced to the fractionation column 110 and/or to the crude acetone product in line 130. As such, in addition to the first column inlet 126 and the second column inlet 127, the fractionation column 110 can also include a third or "water" column inlet 129 coupled thereto. The water in line 128 can be provided at a rate from a low of about 0.01 tons/ton of crude acetone product, about 0.03 tons/ton of crude acetone product, about 0.05 tons/ton of crude acetone product, or about 0.06 tons/ton of crude acetone product to a high of about 0.10 tons/ton of crude acetone product, about 0.15 tons/ton of crude acetone product, about 0.18 tons/ton of crude acetone product, or about 0.20 tons/ton of crude acetone product.

At least a portion of the lower boiling point components of the crude acetone product introduced via line 130 can be recovered via line 140 and processed within an overhead assembly. The overhead assembly can include, but is not limited to, a condenser 142, a separator vessel 148, and a reflux pump 150. The lower boiling point components of the crude acetone product can be recovered via line 140 and introduced to the condenser 142. The condenser 142 can be any suitable type of heat exchanger, such as a shell-and-tube heat exchanger, a cross-flow heat exchanger, or the like. The condenser 142 can be fluidly coupled to line 140 and can receive a coolant or heat transfer medium via line 144. The condenser 142 can thus condense at least a portion of the recovered light components in line 140 and produce cooled light components via line 146. The cooled light components in line 146 can be at least partially condensed to provide a liquid/gas mixture and/or completely condensed to provide a liquid. The coolant delivered via line 144 can include one or more process stream(s). For example, the coolant delivered via line 144 can include one or more process stream(s) recovered from an oxidation unit (not shown). In another example, the coolant via line 144 can include a cumene-containing stream. In a further example, the coolant delivered via line 144 can include at least a portion of a cumene feed to an oxidation unit. At least a portion of the coolant delivered via line 144 to the condenser 142 can originate from a process unit (not shown) fluidly coupled to the fractionation column 110 and a heated coolant via line 184 can be re-introduced to the process unit.

In one or more embodiments, an oxidizer feed via line 171 can be delivered from an oxidizer feed tank 170 to provide at least a portion of the coolant introduced via line 144 to the condenser 142. The oxidizer feed in line 171 can include, but is not limited to, cumene, AMS, water, dimethyl benzyl alcohol (DMBA), CHP, or any combination thereof. In at least one specific embodiment, the oxidizer feed in line 171 can contain a low of about 60 wt %, about 70 wt %, or about 80 wt % to a high of about 90 wt %, about 95 wt %, or about 99 wt % cumene. For example, the amount of cumene in the oxidizer feed in line 171 can be about 85 wt % or more, about 90 wt % or more, about 95 wt % or more, about 96 wt % or more, or about 98 wt % or more. The oxidizer feed in line 171 can contain a low of about 0.1 wt %, about 1 wt %, or about 2 wt % to a high of about 3 wt %, about 4 wt %, or about 5 wt % CHP. The oxidizer feed in line 171 can contain a low of about 0.05 wt %, about 0.1 wt %, or about 0.15 wt % to a high of about 0.3 wt %, about 0.4 wt %, or about 0.5 wt % DMBA. The oxidizer feed in line 171 can contain a low of about 0.01 wt %, about 0.02 wt %, or about 0.03 wt % to a high of about 0.07 wt %, about 0.10 wt %, or about 0.2 wt % water. The oxidizer feed in line 171 can contain a low of about 50 ppmw, about 100 ppmw, or about 150 ppmw to a high of about 200 ppmw, about 500 ppmw, or about 1,000 ppmw AMS.

The use of the oxidizer feed in line 171 can reduce or eliminate fouling within the condenser 142 and associated equipment as compared to the use of water. The oxidizer feed in line 171, can increase the stability of the process, as compared to water and/or air coolants. The use of the oxidizer feed in line 171 can also recover energy that was used to heat an oxidizer feed prior to entering an oxidizer, as compared to a comparative process that is the same except instead of the oxidizer feed in line 171 a coolant of water and/or air is used. For example, the heated oxidizer feed 184 can be delivered to an oxidizer, reducing, or eliminating the duty of an oxidizer feed heat exchanger or heater.

The oxidizer feed in line 171 can be supplied to the oxidizer feed tank 170 from one or more oxidizer feed sources via line 185. The coolant in line 144 supplied to the condenser 142 can be at least about 10%, at least about 20%, at least about 30%, at least about 40%, at least about 50%, at least about 60%, at least about 70%, at least about 80%, or at least about 90% of the oxidizer feed in line 171. In one or more embodiments, the oxidizer feed can provide all of the coolant supplied to the condenser 142.

The oxidizer feed via line 171 can be pumped from the oxidizer feed tank 170 via one or more pumps 172 to produce in a pumped oxidizer feed via line 173. The pumped oxidizer feed via line 173 can be split to form a first oxidizer feed via line 143 and a second oxidizer feed via line 174. The first oxidizer feed via line 143 can be further split to form or provide the coolant via line 144 and an oxidizer feed tank recycle via line 176. The coolant via line 144 can be supplied to the condenser 142 and heat can be indirectly transferred from the light components introduced thereto via line 140 to the coolant to provide the cooled light components via line 146 and a heated coolant via line 145. The heated coolant or first heated coolant via line 145 can be split, equally or unequally, into a second heated coolant via line 177 and a heated oxidizer tank recycle via line 175. The oxidizer feed tank recycle via line 176 and the heated oxidizer tank recycle via line 175 can be combined to form a combined oxidizer feed tank recycle via line 178 that can be introduced to the oxidizer feed tank 170. The oxidizer feed tank recycle can optionally be cooled in a heat exchanger or cooler 179 to produce a cooled oxidizer feed tank recycle via line 180 that can be introduced to the oxidizer feed tank 170. The second heated coolant via line 177 can be combined with the split oxidizer feed in line 174 to provide an oxidizer teed via line 184.

The cooled light components via line 146 can be introduced to a separation vessel 148 to separate an uncondensed gas product or second crude acetone product via line 152 from the cooled light components in line 146. A liquid product or first liquid product via line 151 can be recovered from the separation vessel 148. In one or more embodiments (not shown), at least a portion of the liquid product in line 151 can be recycled as reflux to the fractionation column 110. In one or more embodiments, a second liquid product via line 154 recovered from the separation vessel 148 can be pumped via a reflux pump 150 and recycled via line 156 to the interior volume 112 as reflux to increase column performance. The amount of the condensed light components obtained as the liquid product 151 can be the same or different compared to the amount of the condensed light components obtained as the reflux portion 154. As used herein, the term "reflux ratio" refers to the ratio of amount of condensate returned to a column as reflux 154 to the amount of the crude acetone product in line 130. The reflux ratio can be from a low of about 0.05:1, about 0.13:1, about 0.20:1, or about 0.30:1 to a high of about 0.40:1, about 0.50:1 0.60:1, or about 0.75:1.

Returning to the fractionation column 110, the bottoms product via line 160 can be recovered from the second end 124 thereof. The bottoms product via line 160 can be introduced via line 162 to a reboiler 163. The reboiler 163 can be or include any type of heat exchanger, including a shell-and-tube heat exchanger, cross-flow heat exchanger, or the like. The reboiler 163 can also receive a heat exchange fluid via line 164. For example, the heat exchange fluid via line 164 can be steam provided as an end or side product produced in any other system or device. The steam via line 164 can heat the bottoms product via line 162 in the reboiler 163 to produce a re-heated bottoms product via line 168. The reheated bottoms product via line 168 can then be returned to the fractionation column 110 to provide heat thereto. A portion of the bottoms product via line 160 can also be directed into line 165 for further processing.

The reboiler 163 can be configured to provide various power duties. In one or more embodiments, the reboiler duty can be less if stream 132 is included. For example, the reboiler duty can have a duty that is at least 1% less, at least 3% less, at least 5% less, at least 7% less, at least 10% less, or at least 15% less if stream 132 is included. In another example, the reboiler duty can have a duty that is from about 1% to about 7% less, about 2% to about 5% less, or about 1% to about 10% less if stream 132 is included.

An interior volume 112 of the fractionation column 110 can be empty, partially filled, or completely filled with one or more fill materials (not shown). Illustrative fill materials can include, but are not limited to, trays, packing, or combinations thereof. For example, the fractionation unit 110 can include one or more trays (four are shown: 114, 116, 118, 120). The trays 114, 116, 118, 120 can be representative of four trays among a larger number of trays disposed in the interior volume 112. For example, the total number of trays in the interior volume 112 can be about 45, about 55, about 65, about 75, about 85, or about 95. In another example, the total number of trays disposed within the interior volume 112 can range from a low of about 20, about 30, about 35, about 40, or about 45 to a high of about 55, about 60, about 65, about 70, about 80, about 85, or about 90. The trays 118 and 120 can represent higher number trays. For example, tray 120 can represent the tray nearest the second or "bottom" end 124 of the fractionation column 110.

The trays 114 and 116 can be positioned closer to the first end 122 than the first column inlet 126, and the trays 118, 120 can be disposed closer to the second end 124 than the first column inlet 126. The trays 114, 116, 118, 120 can be positioned closer to the first end 122 than the second column inlet 127. The tray 118 can represent the $15^{th}$ tray of an approximately 65 tray fractionation column 110 numbered from top to bottom with the $1^{st}$ tray being located at the top or first end 122 and the $65^{th}$ tray being located at bottom or second end 124. In an example, the tray 118 can represent the $20^{th}$ or optionally the $30^{th}$ tray of an approximately 65 tray fractionation column 110. The cumene and/or AMS line 132 can be injected between any two adjacent or subsequent trays disposed within the fractionation column 110. For example, the cumene and/or AMS line 132 can be injected between the $40^{th}$ tray 118 and the second end 124 such that the fractionation column 110 can have an increased contact time with the crude AMS in the fractionation column 111. In another example, the cumene and/or AMS line 132 can be injected between any two adjacent or subsequent trays ranging from the $30^{th}$ tray to the $65^{th}$ tray disposed within the fractionation column 110. In another example, the cumene and/or AMS line 132 can be injected through the second column inlet 127 and through a second inlet location (not shown), which can be between any two trays of the fractionation system. In another example, the cumene and/or AMS line 132 can be injected between the $50^{th}$ and $65^{th}$ trays, the $63^{rd}$ and $64^{th}$ trays, the $62^{nd}$ and $63^{rd}$ trays, the $61^{st}$ and $62^{nd}$ trays, the $60^{th}$ and $61^{st}$ trays, the $59^{th}$ and $60^{th}$ trays, the $58^{th}$ and $59^{th}$ trays, the $57^{th}$ and $58^{th}$ trays, the $56^{th}$ and $57^{th}$ trays, the $55^{th}$ and $56^{th}$ trays, the $54^{th}$ and $55^{th}$ trays, the $53^{rd}$ and $54^{th}$ trays, the $52^{nd}$ and $53^{rd}$ trays, the $51^{st}$ and $52^{nd}$ trays, the $50^{th}$ and $51^{st}$ trays, the $49^{th}$ and $50^{th}$ trays, the $48^{th}$ and $49^{th}$ trays, the $47^{th}$ and $48^{th}$ trays, the $46^{th}$ and $47^{th}$ trays, the $45^{th}$ and $46^{th}$ trays, or the $44^{th}$ and $45^{th}$ trays, or a combination thereof. In a further example, the cumene and/or AMS line 132 can be injected at any location of the fractionation column 110 between the lowest tray and the bottom end 124. In an even further example (not shown), the cumene and/or AMS line 132 can be combined with the reheated bottoms product line 168 injected between the lowest tray and the bottom end 124.

The water inlet 129 can be placed on the column at any location above the column inlet 126 or combined with column inlet 126. The tray 114 can be positioned closer to the first end 122 than water inlet 129, while the trays 116, 118, 120 can be disposed between the second end 124 and the water inlet 129. In one example, the tray 116 can represent the $15^{th}$ tray of an approximately 65 tray fractionation column 110. In another example, the tray 116 can represent the $10^{th}$, $11^{th}$, $12^{th}$, $13^{th}$, $14^{th}$, $15^{th}$, $16^{th}$, $17^{th}$, $18^{th}$, $19^{th}$, or $20^{th}$ tray of an approximately 65 tray fractionation column 110. In yet another example, the trays 114, 116, 118, 120 can be part of a stack of trays. The water via line 128 can be injected between any two adjacent or subsequent trays disposed within the fractionation column 110. For example, the water via line 128 can be injected between the $15^{th}$ tray 116 and the first end 122 such that the fractionation column 110 can have an increased contact time with the crude acetone product in the fractionation column 110, thereby reducing the cumene content in the bottoms product via line 160. In another example, the water via line 128 can be injected between any two adjacent or subsequent trays ranging from the $15^{th}$ tray to the $30^{th}$ tray disposed within the fractionation column 110. In another example, water via line 128 can be injected through water inlet 129 and a second location (not shown), which can be between any two trays of the fractionation system above column inlet 126. In another example, the water via line 128 can be injected between the $1^{st}$ and $2^{nd}$ trays, the $2^{nd}$ and $3^{rd}$ trays, the $3^{rd}$ and $4^{th}$ trays, the $4^{th}$ and $5^{th}$ trays, the $5^{th}$ and $6^{th}$ trays, the $6^{th}$ and $7^{th}$ trays, the $7^{th}$ and $8^{th}$ trays, the $8^{th}$ and $9^{th}$ trays, the $10^{th}$ and $11^{th}$ trays, the $11^{th}$ and $12^{th}$ trays, the $12^{th}$ and $13^{th}$ trays, or the $13^{th}$ and $14^{th}$ trays, or a combination thereof. In one specific example, the water via line 128 can be injected between the $14^{th}$ and $15^{th}$ trays.

In at least one specific embodiment, the crude acetone product via line 130 can be introduced to the internal volume 112 of the fractionation column 110 between trays 114 and 120, the cumene and/or AMS via line 132 can be introduced to the internal volume 112 below tray 118, and the water via line 128 can be introduced to the internal volume 112 between tray 114 and the crude acetone product inlet 126. In a more specific embodiment, the crude acetone product via line 130 can be introduced to the internal volume 112 of the fractionation column 110 between trays 116 and 118, the cumene and/or AMS via line 132 can be introduced to the internal volume 112 below tray 118, and water via line 128 can be introduced to the internal volume 112 between trays 114 and 116.

As used herein, the term "trays" can include, but is not limited to, one or more types of trays that can improve the contact between gas and liquid phases within the fractionation column 110. Illustrative trays can include, but are not limited to perforated trays, sieve trays, bubble cap trays, floating valve trays, fixed valve trays, tunnel trays, cartridge trays, dual flow trays, baffle trays, shower deck trays, disc and donut trays, orbit trays, horse shoe trays, cartridge trays, snap-in valve trays, chimney trays, slit trays, or any combination thereof As used herein, the term "packing material" or "packing" can include, but is not limited one or more types of structured and/or random shaped material disposed within the fractionation column 110. The packing material can increase the effective surface area within the fractionation column 110, which can improve the mass transfer between liquid and gas phases within the fractionation column 110. The packing material can be made of any suitable material, for example metals, non-metals, polymers, ceramics, glasses, or any combination thereof. Illustrative examples of random packing material can include, but are not limited to, Raschig rings, Lessing rings, 1-rings, saddle rings, Intalox saddles, Tellerettes, Pall rings, U-rings, or any combination thereof. Illustrative examples of commercially available structured packing can include, but are not limited to, structured packing, corrugated sheets, crimped sheets, gauzes, grids, wire mesh, monolith honeycomb structures, or any combination thereof.

The fill material, e.g., trays 114, 116, 118, 120, can improve mass transfer and/or separation of a multi-component fluid. The fill material and/or the fill pattern in the interior volume 112 can include one or more structured and/or random packed materials. Two or more types of fill material can be disposed within the interior volume 112. For example, the interior volume 112 can contain random dumped packing beneath the first column inlet 126 and one or more trays above the column inlet 126.

The fractionation column 110 can be made of one or more metallic and/or non-metallic materials physically and chemically compatible with the temperature, pressure, and contents of the fractionation column 110. Suitable metallic materials can include, but are not limited to ferrous alloys including carbon and stainless steels such as cladded carbon steel and 304 and 316 stainless steels, and non-ferrous alloys such as aluminum, nickel, tantalum, and the like.

Figure 2:
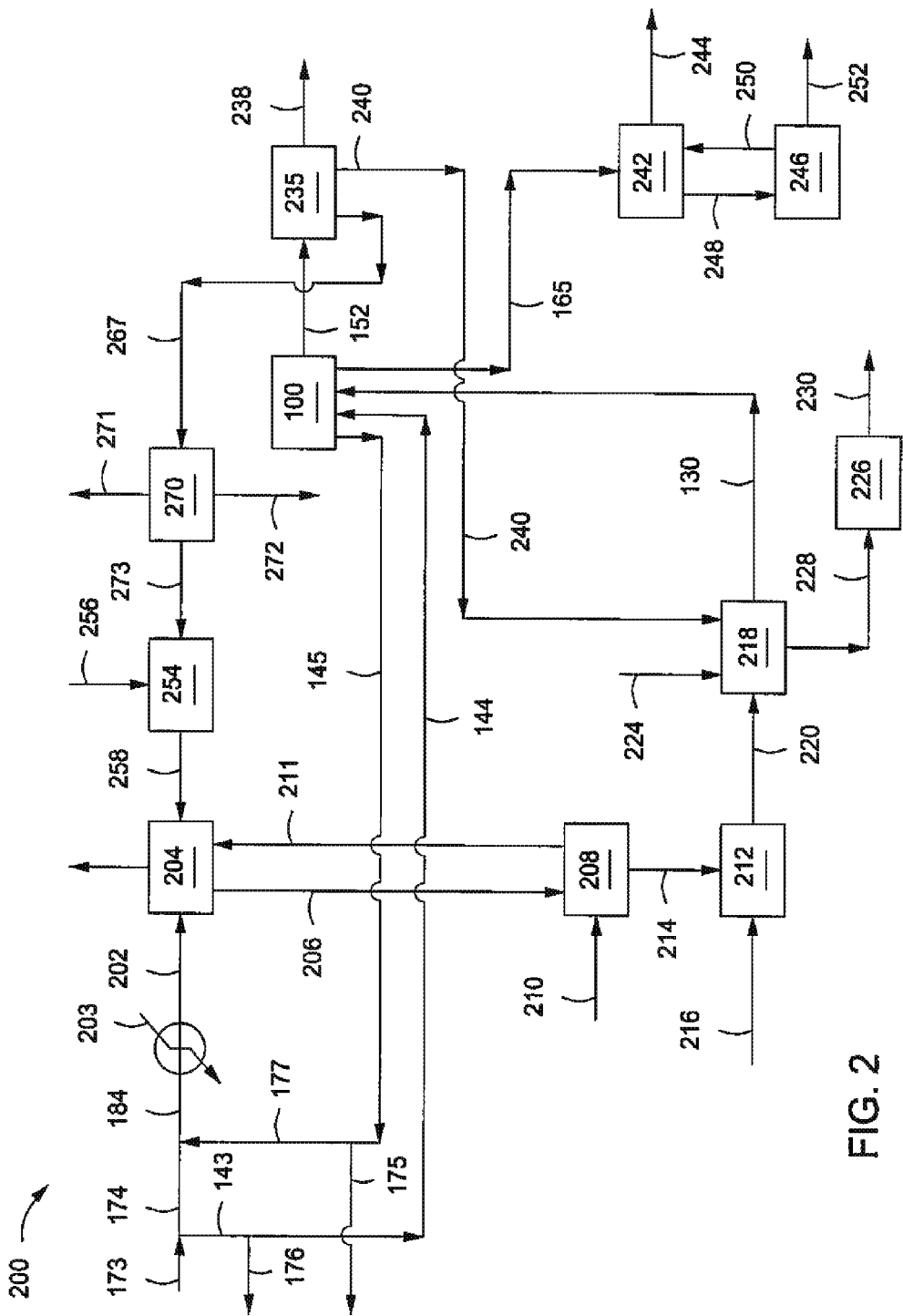
FIG. 2 depicts an illustrative system for producing acetone, according to one or more embodiments described.

FIG. 2 depicts an illustrative system 200 for producing phenol, according to one or more embodiments. A cumene stream via line 202 can be introduced to one or more oxidation units 204. The cumene stream via line 202 can be subjected to heating in a heat exchanger or other heater 203 to produce a heated cumene stream via line 202. The oxidation unit 204 can be any system or device suitable to provide oxygen or any other oxidant to the cumene introduced via line 202. For example, the oxidation unit 204 can be or include one or more bubble or cascade columns. Air, oxygen, or other oxygen containing gas can be added to the bottom of the bubble columns, such that oxygen transfers via the air bubbles into the cumene feed, thereby oxidizing the cumene and forming an oxidized product, which can include CHP, DMBA, acetophenone (ACP), or any combination thereof via line 206. The oxidized product in the line 206 can include from about 10 wt %, about 15 wt %, about 20 wt %, or about 23 wt % to about 25 wt %, about 27 wt %, about 30 wt %, about 35 wt %, or about 40 wt % CHP.

The oxidized product via line 206 can be introduced to one or more concentration units 208 to produce a crude concentrated CHP product via line 214. The concentration unit 208 can be or include one or more vacuum distillation columns, heat exchangers, reflux drums, etc. In such concentration units 208, cumene can be separated at temperatures below about 100° C., for example. Additional cumene can be added via line 210 and introduced as reflux to one or more of the vacuum distillation columns to improve cumene separation performance. Further, such additional cumene can be provided for safety, for example, during shutdowns. The cumene obtained from the concentration units 208 can be recycled via line 211 back to the oxidizer 204 to augment the cumene feed introduced via line 202, while the crude concentrated CHP product can be recovered via line 214. The crude concentrated CHP product in line 214 can include from about 60 wt %, about 70 wt %, about 80 wt %, or about 81 wt % to about 83 wt %, about 85 wt %, about 90 wt %, or about 95 wt % of CHP.

The crude concentrated CHP via line 214 can be introduced to one or more cleavage units 212. One or more acids via line 216 can also be introduced to the cleavage unit 212. A suitable acid that can be introduced via line 216 to the cleavage unit 212 can include, but is not limited to, sulphuric acid. The cleavage unit 212 can include a circulation loop (not shown) with one or more heat exchangers included therein. The crude concentrated CHP can be introduced to the circulation loop to produce acetone and phenol. Further, the cleavage reaction can be exothermic, thus the heat exchangers can be provided with cooling water or another heat exchange fluid to control the temperature of the concentrated feed in the cleavage unit 212. In the cleavage unit 212, DMBA can be partially dehydrated to AMS, which can react in consecutive reactions with phenol to form cumylphenols. AMS can also form high-boiling point dimers in the cleavage unit 212. DMBA reacts with CHP to form dicumyl peroxide (DCP) and water. Additional byproducts can also produced, such as hydroxyacetone, 2-methylbenzofurane (2 MBF), and diacetone alcohol. These products can be fed to a plug-flow reactor (not shown), for example, at temperatures of about 100° C. or more. In the plug flow reactor, DCP can decompose to AMS, phenol, and acetone. Also in the plug flow reactor, DMBA can be dehydrated to AMS and water. At least a portion of these products can be discharged from the cleavage unit 212 as a crude product feed via line 220. One example of a cleavage unit can be as discussed and described in U.S. Pat. No. 5,371,305.

The crude product feed via line 220 can be introduced to one or more neutralization units 218, where one or more salt solutions, for example, sodium phenate, can be introduced via line 224 to reduce, substantially reduce, or terminate any continuing cleavage reactions. At least a portion of the neutralized crude product via line 228 can be introduced to one or more dephenolation units 226. Phenol can be removed or separated from the neutralized crude product within the dephenolation unit 226 using any suitable process. For example, the phenol can be separated via liquid-liquid separation using cumene as an extraction solvent. The recovered phenol can be in the form of sodium phenate, which can be returned to the neutralization unit 218. From the dephenolation unit 226, waste water via line 230 can be discharged for further processing and/or disposal.

Returning to the neutralization unit 218, the crude acetone product or a neutralized crude acetone product via line 130, which can include acetone and cumene, can be introduced via line 130 (see also FIG. 1) to the fractionation system 100. One or more acetone fractionation units 235 can be in fluid communication with the fractionation system 100. The acetone fractionation unit(s) 235 can be or include one or more distillation columns. In the fractionation system 100 acetone can be separated as a top product and/or an upper side-stream via line 152 (see FIG. 1). The acetone via line 152 can be subjected to the acetone fractionation unit(s) 235 to obtain acetone via line 238. The acetone via line 238 can be directed back to the cleavage unit 212 (not shown), can be directed to a storage container or can be otherwise stored or processed for subsequent use. Further, a base, such as caustic soda, can be added to the acetone fractionation unit 235 to convert aldehydes to high-boiling components.

A phenol rich bottoms product 165 recovered from the fractionation system 100 can be recovered and/or subjected to further processing. In another example (not shown), the bottoms product from the crude acetone column can be sent to a cumene column, which can also be part of the acetone fractionation unit(s) 235. In an example (not shown), at least a portion of the bottom product via line 267 can be recycled to the fractionation system 100 via line 132. One example of an acetone fractionation unit can be as discussed and described in U.S. Pat. No. 4,340,447.

The bottoms from the fractionation system 100 can be directed to a phenol fractionation unit 242 via line 165. An aqueous bottoms from the acetone fractionation unit 235 can be introduced or recycled to the neutralization unit 218 via line 240. The phenol fractionation unit 242 can additionally include one or more heat exchangers (e.g., condensers, reboilers, etc.), reflux barrels, pumps, and the like. The phenol fractionation unit 242 can instead or in addition include one or more adsorption units, purification units, or the like suitable to recover phenol from the hydrocarbon feed in line 165. The phenol fractionation unit 242 can thus recover a phenol product via line 244, which can be directed to a storage container or otherwise processed, purified, conditioned, stored for downstream use. The phenol can, for example, be converted to bis-phenol-A (BPA) to produce polycarbonate and/or phenolic resins.

A remaining heavy hydrocarbon product via line 248 can be directed to one or more heavy removal units 246. The heavy removal unit 246 can be a distillation column, for example, operated at a higher temperature than the phenol fractionation unit 242. Hydrocarbons vaporized in the heavy removal unit 246 can be recycled back to the phenol fractionation unit 242 via line 250, such that additional phenol remaining in the line 248 can be recovered. Remaining heavy hydrocarbons via a line 252 can be removed for further processing, disposal, combustion, etc.

Returning to the acetone fractionation unit(s) 235, a hydrocarbon bottoms product from the acetone fractionation unit(s) 235 via line 267 can be directed to the AMS fractionation system 270. In the AMS fractionation system 270, a light hydrocarbon via line 271 can be recovered, a heavy hydrocarbon via line 272 can be recovered, and a side-stream mixture of AMS and cumene via line 273 can be recovered.

The side-stream mixture of AMS and cumene via line 273 can be directed to one or more hydrogenation units 254 and mixed with hydrogen via line 256. The hydrogenation unit 254 can include a reactor having one or more selective palladium, nickel, or other catalysts therein. The catalysts, in combination with a flow of hydrogen via line 256, can cause the AMS to hydrogenate to form cumene, without interfering hydrogenation of remaining phenol. Such phenol can then be removed via a cumene scrubber (not shown). The AMS and cumene mixture can thus be converted to a substantially cumene feed, which can be recycled back to the oxidation unit 204 via a line 258. A suitable hydrogenation unit can be as discussed and described in U.S. Pat. No. 7,381,854. In an example (not shown), at least a portion of line 273 can be recycled to the fractionation system 100. In another example (not shown), at least a portion of line 258 can be recycled to the fractionation system 100.

Referring now to FIGS. 1 and 2, in one or more embodiments, at least a portion of the cumene stream in line 173 can be introduced into a coolant stream 143, 144 for providing coolant to a condenser 142 in the overhead assembly of the fractionation system 100. A heated coolant stream via line 145 leaving the condenser 142 can return to the cumene stream in line 174 proximate line 184 and can subsequently be introduced into the oxidizer 204 via line 202 after further heating in heat exchanger 203. The heated coolant stream via line 145, 177 can return to the cumene stream in line 174, at any point downstream from where at least a portion of the cumene stream via line 173 can be introduced into the coolant stream 144. In an example (not shown), at least a portion of a substantially cumene feed via line 258, can be introduced into the coolant stream 185 in order to provide coolant to the condenser 142. The heated coolant via line 145 leaving the condenser 142 can re-enter the substantially cumene feed line 258 and can subsequently be introduced into the oxidizer 204. In another example (not shown), at least a portion of the fresh cumene feed via line 202 can be introduced into the coolant stream 144 in order to provide coolant to the condenser 142. In a further example (not shown), the heated coolant via line 145 leaving the condenser 142 can re-enter the fresh cumene feed line 210 and can subsequently be introduced into the concentration unit 208.

The heater 203 can be disposed at any location on line 202. For example, the heater 203 can be disposed downstream from where the coolant stream via line 144 is withdrawn from the cumene stream in line 173 and at or upstream of where the heated coolant stream via line 145 is re-introduced to the cumene stream in line 184. In an example (not shown), the cumene stream via lines 143, 144 can be heated in heater 203. In a further example, the heater 203 can be disposed downstream from where the heated coolant stream via line 145 is re-introduced to the cumene stream via line 184. In one or more embodiments, the re-introduction of the heated coolant stream via line 184 can reduce or eliminate the need for the heater 203. In operation from about 10% to about 95%, from about 25% to about 85%, or from about 50% to about 75% of total heat supplied to the cumene stream via line 202 can be provided by the heated coolant stream in lines 145 by introduction of the heated coolant stream via line 184 to line 202.

Embodiments of the present disclosure further relate to any one or more of the following paragraphs:

1. A method for fractionating a crude acetone, comprising: introducing a crude acetone comprising acetone and phenol to a fractionation column; introducing cumene, AMS, or a combination thereof to the fractionation column; fractionating the crude acetone within the fractionation column to produce an acetone containing overhead and a phenol containing bottoms; and condensing at least a portion of the acetone containing overhead indirectly with a cool heat transfer medium to provide a condensed crude acetone product and a heated heat transfer medium, wherein the heat transfer medium comprises cumene.

2. The method according to paragraph 1, wherein the cumene, AMS, or combination thereof is introduced to the fractionation column below a location where the crude acetone is introduced to the fractionation column.

3. The method according to paragraphs 1 or 2, wherein the cumene, AMS, or a combination thereof is introduced to the fractionation column at a location proximate a bottom end of the fractionation column.

4. The method according to any one of paragraphs 1 to 3, wherein the crude acetone comprises hydroxyacetone, and wherein a greater amount of the hydroxyacetone leaving the fractionation column is recovered in the overhead than in the bottoms product.

5. The method according to any one of paragraphs 1 to 4, wherein the crude acetone is a downstream product of the cooling medium.

6. The method according to any one of paragraphs 1 to 5, wherein the crude acetone has a pH from about 4 to about 7.

7. The method according to any one of paragraphs 1 to 6, further comprising introducing at least a portion of the condensed crude acetone product to the fractionation column as a reflux, wherein the reflux to crude acetone feed is at a reflux to feed ratio of less than 0.60:1.

8. The method according to any one of paragraphs 1 to 7, wherein the heat transfer medium comprises from about 80 wt % to about 99 wt % cumene and the method further comprises introducing the heated heat transfer medium to an oxidation unit to produce an oxidized product comprising cumene hydro-peroxide (CHP).

9. A method for producing acetone, comprising: introducing an oxidant and a first cumene containing stream to an oxidation unit to produce an oxidized cumene hydro-peroxide (CHP) product; introducing the oxidized CHP product and a second cumene containing stream to a concentration unit to produce a concentrated CHP product; introducing the concentrated CHP product to a cleavage unit to produce a crude acetone; introducing the crude acetone to a neutralization unit to produce a neutralized crude acetone; introducing the neutralized crude acetone, cumene, and AMS to a fractionation column to produce an acetone containing overhead and a bottoms product comprising phenol; and introducing the acetone containing overhead and a coolant comprising at least a portion of the first cumene containing stream to a condenser.

10. The method according to paragraph 9, wherein the cumene and AMS is introduced to the fractionation column at a location on the fractionation column below where the neutralized crude acetone product is introduced to the fractionation column.

11. The method according to paragraphs 9 or 10, further comprising withdrawing a heated coolant from the condenser and introducing the heated coolant to the first cumene containing stream prior to introducing the first cumene containing stream to the oxidation unit.

12. The method according to any one of paragraphs 9 to 11, further comprising recycling at least a portion of the crude acetone overhead to the oxidation unit.

13. The method according to any one of paragraphs 9 to 12, wherein the neutralized crude acetone comprises hydroxyacetone, and wherein a greater amount of the hydroxyacetone leaving the fractionation column is recovered in the overhead than in the bottoms product.

14. A system for separating a phenol and acetone mixture, comprising: a fractionation column; a first column inlet configured to introduce a crude acetone product comprising phenol and acetone to an internal volume of the fractionation column; a second column inlet configured to introduce a feed comprising cumene, alpha-methyl styrene, or a mixture thereof to the internal volume of the fractionation column; a column overhead line fluidly coupled to the fractionation column and configured to recover a light hydrocarbon product comprising acetone therefrom; a condenser fluidly coupled to the column overhead line and configured to exchange heat between the light hydrocarbon product and a coolant to provide a cooled light hydrocarbon and a heated coolant, wherein the coolant is in fluid communication with the first column inlet; and a bottoms line fluidly coupled to the fractionation column, proximal the bottom thereof, and configured to remove a heavy hydrocarbon product comprising phenol therefrom.

15. The system according to paragraph 14, wherein the coolant is fluidly isolated from the light hydrocarbon within the condenser.

16. The system according to paragraphs 14 or 15, wherein the fractionation column is oriented substantially vertically, and wherein the second column inlet is located on the fractionation column at a point below where the first column inlet is located on the fractionation column.

17. The system according to any one of paragraphs 14 to 16, further comprising a plurality of trays within the internal volume of the fractionation column, wherein the second column inlet is located on the fractionation column at a point below the plurality of trays.

18. The system according to any one of paragraphs 14 to 17, wherein the coolant and heated coolant are in fluid communication with the first column inlet.

19. The system according to any one of paragraphs 14 to 18, wherein the fractionation column is in fluid communication with a neutralization unit.

20. The system according to any one of paragraphs 14 to 19, wherein the coolant line to the condenser is in fluid communication with an oxidation unit.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for fractionating a crude acetone, comprising:
introducing a crude acetone comprising acetone and phenol to a fractionation column;
introducing cumene, AMS, or a combination thereof to the fractionation column;
fractionating the crude acetone within the fractionation column to produce an acetone containing overhead and a phenol containing bottoms; and condensing at least a portion of the acetone containing overhead indirectly with a cool heat transfer medium to provide a condensed crude acetone product and a heated heat transfer medium, wherein the heat transfer medium comprises cumene.

2. The method of claim 1, wherein the cumene, AMS, or combination thereof is introduced to the fractionation column below a location where the crude acetone is introduced to the fractionation column.

3. The method of claim 1, wherein the cumene, AMS, or a combination thereof is introduced to the fractionation column at a location proximate a bottom end of the fractionation column.

4. The method of claim 1, wherein the crude acetone comprises hydroxyacetone, and wherein a greater amount of the hydroxyacetone leaving the fractionation column is recovered in the overhead than in the bottoms product.

5. The method of claim 1, wherein the crude acetone is a downstream product of the cooling medium.

6. The method of claim 1, wherein the crude acetone has a pH from about 4 to about 7.

7. The method of claim 1, further comprising introducing at least a portion of the condensed crude acetone product to the fractionation column as a reflux, wherein the reflux to crude acetone feed is at a reflux to feed ratio of less than 0.60:1.

8. The method of claim 1, wherein the heat transfer medium comprises from about 80 wt % to about 99 wt % cumene and the method further comprises introducing the heated heat transfer medium to an oxidation unit to produce an oxidized product comprising cumene hydro-peroxide (CHP).

9. A method for producing acetone, comprising:
introducing an oxidant and a first cumene containing stream to an oxidation unit to produce an oxidized cumene hydro-peroxide (CHP) product;
introducing the oxidized CHP product and a second cumene containing stream to a concentration unit to produce a concentrated CHP product;
introducing the concentrated CHP product to a cleavage unit to produce a crude acetone;
introducing the crude acetone to a neutralization unit to produce a neutralized crude acetone;
introducing the neutralized crude acetone, cumene, and AMS to a fractionation column to produce an acetone containing overhead and a bottoms product comprising phenol; and
introducing the acetone containing overhead and a coolant comprising at least a portion of the first cumene containing stream to a condenser.

10. The method of claim 9, wherein the cumene and AMS is introduced to the fractionation column at a location on the fractionation column below where the neutralized crude acetone product is introduced to the fractionation column.

11. The method of claim 9, further comprising withdrawing a heated coolant from the condenser and introducing the heated coolant to the first cumene containing stream prior to introducing the first cumene containing stream to the oxidation unit.

12. The method of claim 9, further comprising recycling at least a portion of the crude acetone overhead to the oxidation unit.

13. The method of claim 9, wherein the neutralized crude acetone comprises hydroxyacetone, and wherein a greater amount of the hydroxyacetone leaving the fractionation column is recovered in the overhead than in the bottoms product.

14. A system for separating a phenol and acetone mixture, comprising:
a fractionation column;
a first column inlet configured to introduce a crude acetone product comprising phenol and acetone to an internal volume of the fractionation column;
a second column inlet configured to introduce a feed comprising cumene, alpha-methyl styrene, or a mixture thereof to the internal volume of the fractionation column;
a column overhead line fluidly coupled to the fractionation column and configured to recover a light hydrocarbon product comprising acetone therefrom;
a condenser fluidly coupled to the column overhead line and configured to exchange heat between the light hydrocarbon product and a coolant to provide a cooled light hydrocarbon and a heated coolant, wherein the coolant is in fluid communication with the first column inlet; and
a bottoms line fluidly coupled to the fractionation column, proximal the bottom thereof, and configured to remove a heavy hydrocarbon product comprising phenol therefrom.

15. The system of claim 14, wherein the coolant is fluidly isolated from the light hydrocarbon within the condenser.

16. The system of claim 14, wherein the fractionation column is oriented substantially vertically, and wherein the second column inlet is located on the fractionation column at a point below where the first column inlet is located on the fractionation column.

17. The system of claim 16, further comprising a plurality of trays within the internal volume of the fractionation column, wherein the second column inlet is located on the fractionation column at a point below the plurality of trays.

18. The system of claim 14, wherein the coolant and heated coolant are in fluid communication with the first column inlet.

19. The system of claim 14, wherein the fractionation column is in fluid communication with a neutralization unit.

20. The system of claim 14, wherein the coolant line to the condenser is in fluid communication with an oxidation unit.

* * * * *